United States Patent [19]

Zhao et al.

[11] Patent Number: 5,106,371
[45] Date of Patent: Apr. 21, 1992

[54] CLINICAL SYRINGE TO BE RENDERED USELESS AFTER BEING USED ONCE

[76] Inventors: Mo Zhao, Renmin Road, Shaping Heshan; Zhao Shaojun, 2/F 36 Shuyuan, Jianmen, both of Guangdong, China

[21] Appl. No.: 661,908

[22] Filed: Feb. 27, 1991

[30] Foreign Application Priority Data

Feb. 28, 1990 [CN] China ............ 90101139.8
Sep. 19, 1990 [CN] China ............ 90107953.7
Jan. 30, 1991 [CN] China ............ 91100691.5

[51] Int. Cl.$^5$ ............................................. A61M 5/00
[52] U.S. Cl. ............................................. 604/110; 604/218
[58] Field of Search ............ 604/110, 187, 218, 228

[56] References Cited

U.S. PATENT DOCUMENTS

| | | | |
|---|---|---|---|
| 4,233,975 | 11/1980 | Yerman . | |
| 4,687,467 | 8/1987 | Cygielski | 604/110 |
| 4,713,056 | 12/1987 | Butterfield | 604/110 |
| 4,826,483 | 5/1989 | Molnar, IV | 604/110 |
| 4,863,427 | 9/1989 | Cocchi | 604/218 X |
| 4,874,372 | 10/1989 | McArthur et al. | 604/110 |
| 4,880,410 | 11/1989 | Rossmark | 604/110 |
| 4,883,466 | 11/1989 | Glazier | 604/110 |
| 4,923,443 | 5/1990 | Greenwood et al. | 604/110 |

*Primary Examiner*—John D. Yasko
*Attorney, Agent, or Firm*—Baker & Daniels

[57] ABSTRACT

The present invention provides a clinical syringe to be rendered useless after being used once. It comprises a barrel with a needle fitting hub, a piston sealingly and slidably fitted within the barrel and a piston rod connected to the piston. The piston head is provided with a resilient detent plug with a slot thereon, and an injection opening is defined at a position of the barrel corresponding to the detent plug, the diameter of which is smaller than the inner diameter of the needle fitting hub. A U-shaped notch is punched at the top surface of the piston head adjacent the detent plug to form a U-shaped tongue. If the piston rod is to be pulled back after the syringe being used once, the piston head would be torn at the U-shaped notch due to the retaining of the detent plug by the bottom surface of needle fitting hub, rendering it incapable of drawing the injection fluid.

12 Claims, 4 Drawing Sheets

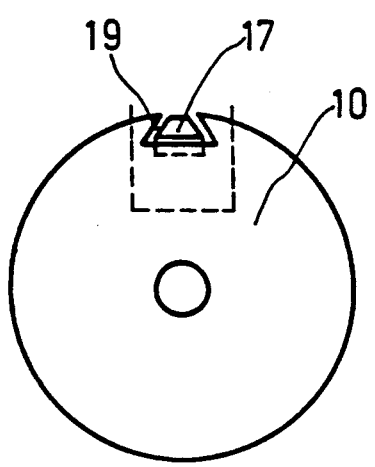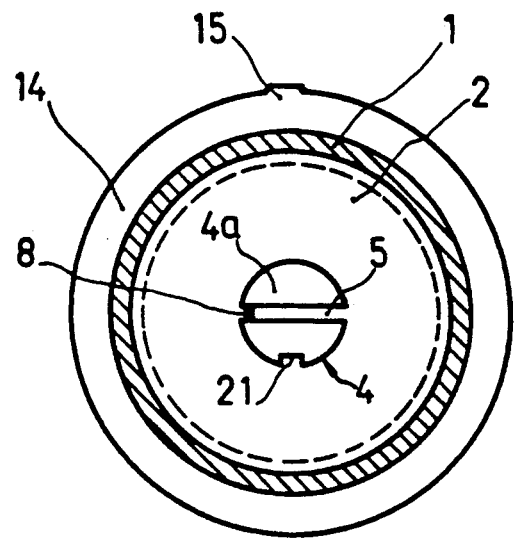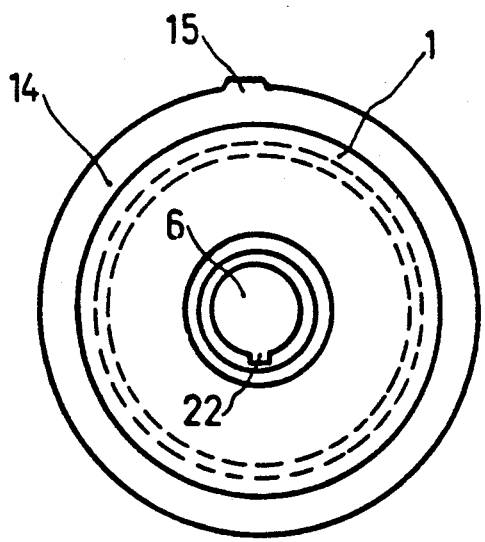

CLINICAL SYRINGE TO BE RENDERED USELESS AFTER BEING USED ONCE

The present invention relates to a novel clinical syringe, particularly a non-reusable syringe.

Conventional clinical syringe includes a barrel, a piston sealingly and slidably fitted within the barrel and a piston rod connected to the piston, as well as a needle. The piston with is position rod of this type of syringe is capable of sliding back and forth freely within the barrel without damaging in the least the syringe and so is the syringe reusable. The defect of this type of syringe is that owing to the reusableness of the syringe, it is subject to cross infection of diseases among diseased individuals.

The object of the present invention is to provide a clinical syringe to be rendered useless after being used once to overcome the above-mentioned defect.

To attain the above-mentioned object, a clinical syringe to be rendered useless after being used once according to the present invention, comprises a barrel with a needle fitting hub at the middle of its front end, a piston sealingly and slidably fitted within the barrel and a piston rod connected to the piston, characterized in that a resilient detent plug with a slot thereon is provided at the piston head, an injection opening is defined at a position of the barrel corresponding to the detent plug, the diameter of which is smaller than inner diameter of the needle fitting hub; the dimensions of the slot and the injection opening as well as the shape and dimension of the resilient detent plug are designed in such a manner that when the piston is pushed forward, the resilient detent plug can easily pass through the injection opening and when it passes through the opening, the injection fluid can still flow through the injection opening, and when the injection is finished, if the piston rod is to be retracted after being used once, the detent plug will be retained by the injection opening due to the restoration of the detent plug, and thus unable to get back into the barrel through the opening; said piston rod is a hollow rod or said piston rod is hollow only at its one end which is connected to the piston, radial apertures opening into the piston rod bore are defined in the hollow part of that rod; in order to render the syringe destroyed completely after being used once, that is, causing the piston ante-chamber in the barrel to communicate with the piston rear chamber and/or with the outside atmosphere by means of the piston rod bore and the radial apertures so that new injection fluid can not be drawn, the connection between the piston head and the resilient detent plug should be so designed that upon retracting the piston rod, it will easily be destroyed due to the retaining of the detent plug.

In addition, one or more longitudinal cutouts can be defined on the periphery of the resilient detent plug or the injection opening of the barrel, so that injection fluid can still flow through the injection opening when the detent plug passes through the injection opening.

Preferred embodiments of the present invention will now be described, by way of example only, with reference to the accompanying drawings, wherein;

FIG. 4 is a diagrammatic view of the end plate of the piston rod seen in the direction opposite to the direction C in FIG. 1;

FIG. 5 is an enlarged section view similar to FIG. 2, showing a variant of the resilient detent plug shown in FIG. 2;

FIG. 6 is an enlarged diagrammatic view of the front end of the syringe seen in the direction D in FIG. 1, showing the injection opening of the barrel with a longitudinal groove defined on its periphery, the groove being adapted in the case where the slot in the resilient detent plug has a uniform width;

Figure 1:
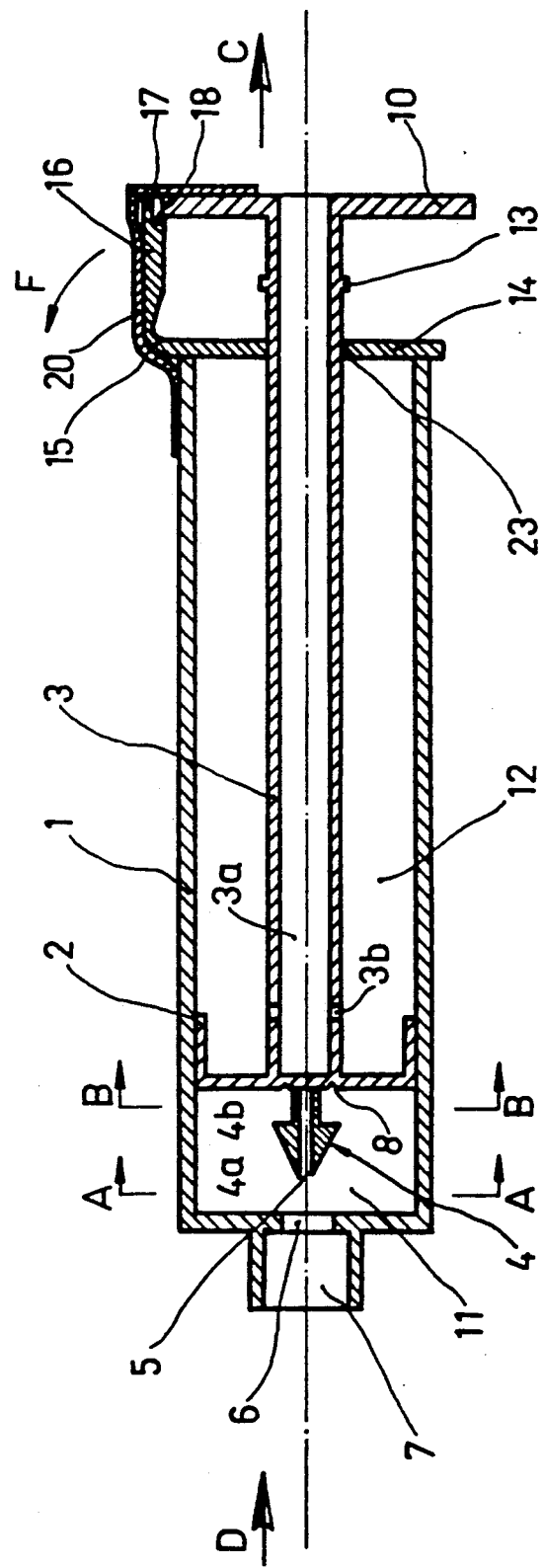
FIG. 1 is a diagrammatic longitudinal sectional view of the construction of a syringe according to the present invention.
Figure 2:
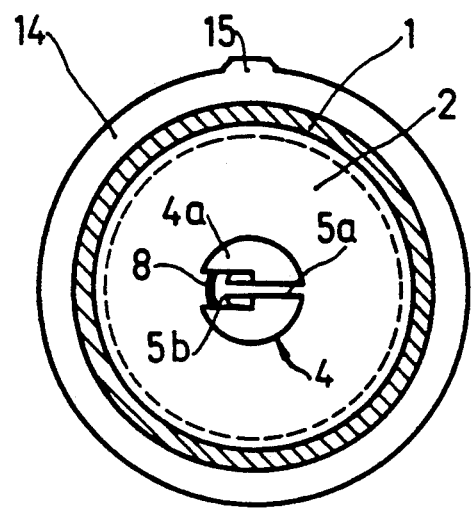
FIG. 2 is an enlarged sectional view along line A—A in FIG. 1, showing the shape and position of the slot formed in the resilient detent plug.
Figure 3:
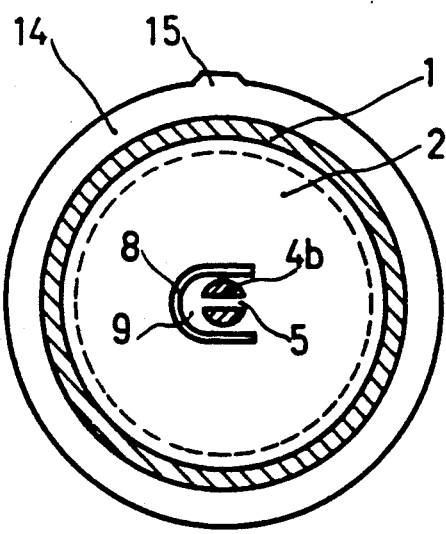
FIG. 3 is an enlarged sectional view along line B—B in FIG. 1, showing the U-shaped notch punched on the piston head.

The syringe shown in FIG. 1 comprises a barrel 1 with a needle fitting hub 7 at the middle of its front end, a piston 2 sealingly and slidably fitted within the barrel and a piston rod 3 connected to the piston A resilient detent plug 4 with a longitudinal slot 5 is defined at the piston head, which slot 5 is made up of slots 5a and 5b of different width, as shown in FIG. 2. At a position of the barrel corresponding to the detent plug 4 is provided an injection opening 6 with a diameter smaller than inner diameter of the needle fitting hub 7. The resilient detent plug 4 is made up of a conic body 4a with a radial dimension at the conic bottom greater than the diameter of the injection opening 6 but smaller than the inner diameter of the needle fitting hub 7, and a supporting rod 4b which connects the conic body with the piston head and has a radial dimension smaller than or equal to the diameter of the injection opening 6. The resilient detent plug 4 is preferably formed integral with the piston 2, and slot 5 is preferably located in the plane of symmetry of the conic body and extends from the conic body to within the supporting rod. In the case that the supporting rod is very slender, the slot 5 can only have the wide portion 5b provided in the conic body 4a. The dimensions of the slot 5, the injection opening 6 and the conic body 4a of the resilient detent plug are so designed that when the piston 2 is pushed forward forcing the detent plug 4 into the injection opening 6, the detent plug 4 is squeezed to undergo an elastic deformation as the diameter of the injection opening 6 is smaller than the diameter of the bottom of the conic body 4a. At this time the norrow portion 5a of the slot 5 is squeezed to close so that the deformed bottom of the conic body can just pass through the injection opening 6. When the norrow portion 5a is closed, owing to the existence of the wide portion 5b of the slot 5, the injection fluid in the barrel can still be driven through the injection opening 6 via the portion 5b into the needle fitting hub 7, to successfully carry out the injection process. When the conic body 4a of the detent plug 4 entirely passes through the injection opening 6, as the diameter of the conic body 4a of the detent plug 4 is smaller than the inner diameter of the needle fitting hub 7, the detent plug 4 can fully or partially restore through its inherent elasticity. After restoration, the diameter of the bottom of the conic body is slightly greater than the diameter of the injection opening 6, so that the injection opening 6 can effectively retain the detent plug 4, thereby the piston and piston rod can not slide freely backward in the barrel. At this time the injection fluid is just being drained away, and the whole injection process is completed. A non-through U-shaped notch 8 can be punched at the top surface of the piston head adjacent said detent plug 4 to form a U-shaped tongue 9, as shown in FIG. 3. When the conic body 4a of the detent plug 4 passes through the injection opening 6 and gets into the needle fitting hub 7 (i.e., injection is completed), if the end plate 10 of the piston rod is retracted (i.e., attempting to reuse the syringe), the piston rod 3 connected with the end plate 10 will tend to draw the piston 2 backward, thus tearing the piston head at the U-shaped notch 8 under the pulling force of the conic body 4a of the detent plug retained by the bottom surface of the needle fitting hub 7, so that chamber 11 of the barrel communicates with chamber 12 through the bore 3a and apertures 3b of the piston rod 3, thus disabling the piston through damaged, rendering the whole syringe useless.

Alternatively, the piston head may be provided with an opening communicating with the piston rod bore 3a and at the lower end of the resilient detent plug, that is, at the lower end of the supporting rod 4b is provided a thin piece adapted to cover completely said piston opening. The thin piece together with the resilient detent plug 4 is attached hermetically to the piston head. After the syringe has been used once, upon retracting the piston rod, the detent plug will be retained inside the needle fitting hub 7, so that the detent plug is torn away from the piston head together with the thin piece, or the thin piece is damaged. Alternatively, screw threads can be provided in said piston opening and at the lower end of the resilient detent plug respectively, so that the detent plug can be sealingly threaded in said opening of the piston head; upon retracting the piston rod at the time when the detent plug, is retained inside the needle fitting hub 7 of the barrel, the detent plug would be pulled asunder from the piston opening.

When the syringe is to effect an injection, the injector must exert a slightly stronger pushing force when the conic body 4a gets into the injection opening 6, to cause the detent plug 4 to undergo an elastic deformation so that the conic body 4a can pass through the injection opening 6 and get into the needle fitting hub 7. Therefore, it is necessary to remind the injector at the time when the conic body starts to get into the injection opening. To attain this, a flange 13 is provided around the piston rod as a indicating means. Its position on the piston rod should be such that when the conic body gets into the injection opening 6 and is being squeezed by that opening, the flange 13 just reaches the outer surface of the end wall 14 of the barrel. The injector at this time should exert a slightly stronger pushing force to push the flange passing through the end wall, thereby forcing the conic body 4a of the detent plug 4 to pass through the injection opening 6.

To guard against the case that the syringe, before being used, is rendered useless through inadvertent pushing forward the piston to force the conic body 4a of the detent plug 4 to pass through the injection opening 6, a spacer bar 16 is provided on the barrel end wall of the syringe of the present invention, one end of which is connected to the barrel end wall by an resilient connecting means 15. When no external force is applied, the resilient connecting means 15 causes the spacer bar 16 to form an acute or right angle with the piston rod 3. At this position, the spacer bar will not prevent the piston rod from normal sliding. When an external force is applied opposite to the direction F shown in FIG. 1 to the spacer bar 16 (for example, manipulated by hand), the resilient connecting means 15 will be bent upward to place the spacer bar to a position parallel to the piston rod 3. The free end of the spacer bar is designed to have a dovetail shaped tongue 17 with a stop shoulder 18. A dovetail groove 19 is defined in the end plate 10 of the piston rod 3. When the spacer bar 16 is in the position parallel to the piston rod 3, that is, in the engaging position, the tongue 17 engages within the groove 19 (as shown in FIG. 1 and 4). At this point, even if the external force is released, the restoring moment of the resilient connecting means 15 will not enable the spacer bar 16 to move in the direction of F back to its original position. This is because the dovetail groove 19 prevents the outward movement of the dovetail tongue. Moreover, as the dovetail tongue 17 on the free end of the spacer bar 16 is provided with the stop shoulder 18, the engagement of the tongue 17 with the groove 19 will prevent the end plate 10 of the piston rod 3 from being pushed forward. Consequently, the spacer bar 16 in the engaging position serves as means of guarding against inadvertent pushing forward of the piston rod. In order to prevent the end plate 10 of the piston rod from sliding backward from its mounting position, a sealing tape 20 is attached to (for example, stuck to )the end plate 10 with its one end and to the spacer bar 16 and/or the end of the barrel with the other end. As will be seen that the above-mentioned stop shoulder 18 and the sealing tape 20 ensure that the piston rod 3 will not be allowed to effect any erroneous movement as long as the spacer bar 16 and the end plate 10 are in their engaged position. When the syringe is not in use, the Space bar 16 and the end plate 10 are in the above-mentioned engaging position and are attached with sealing tape 20. During use, as long as the sealing tape 20 is removed, the syringe can be employed to draw injection fluid, that is, the end plate 10 lugs the piston rod 3 to move in the direction C in FIG. 1. At this time the tongue 17 is disengaged from the groove 19 and the spacer bar 16 under the action of restoring moment goes back in the direction F as shown in FIG. 1 to its initial position, no longer hindering the end plate 10 from being pushed forward, so that the syringe could be used in a normal way.

Moreover, the end wall 14 of the barrel can be adhered to the barrel by adhesive, or secured thereto through threaded sections provided respectively in the barrel and on the end plate. The spacer bar 16 can be formed integral with the end wall 14 and the resilient connecting means 15 can be formed in the junction of the end wall and the spacer bar by having part of material thereat cut away. Furthermore, said conic body can also be an oblate conic body or conic body of any other shape.

Referring now to FIG. 5, it shows a variant of the conic body 4a of the detent plug 4 as shown in FIG. 2. The difference resides in that the width of its slot 5 is uniform throughout, a longitudinal cutout 21 is formed on the peripheral edge of the conic body 4a, in a plane perpendicular to the plane of symmetry where the slot 5 lies. Thus, when the conic body 4a passes through the injection opening causing the slot 5 to close, the injection fluid can still be squeezed out from the barrel through that cutout 21.

Referring now to FIG. 6, a longitudinal cutout 22 is provided at any place. On the peripheral edge of the injection opening 6. In this case there might be no such above-mentioned cutout 21 as shown in the variant of the conic body 4a of FIG. 5. When the slot 5 is closed, the injection fluid can be squeezed out from the barrel through the cutout 22 in the injection opening 6.

Figure 7:
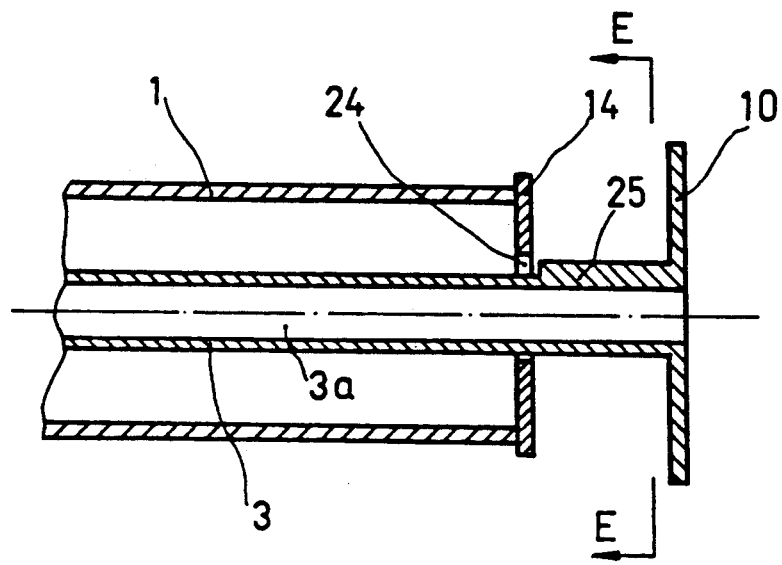
FIG. 7 is a fragmentary longitudinal sectional view of the rear end of the syringe according to the present invention, showing an alternative type of inadvertent push preventive structure.
Figure 8:
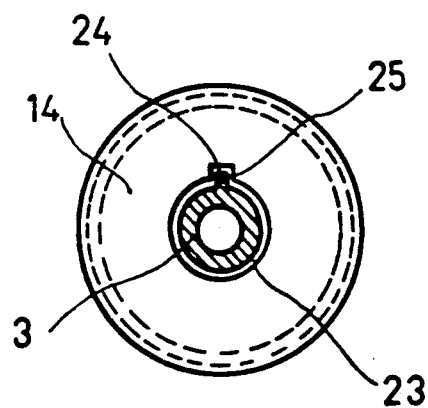
FIG. 8 is a sectional view along line E—E in FIG. 7, showing the rib on the piston rod aligned with the groove of the opening on the end wall of the barrel.

Referring now to FIG. 7, it shows another embodiment of an inadvertent push preventive structure. A longitudinal cutout 24 similar to the cutout 22 at the peripheral edge of the injection opening shown in FIG. 6 is formed at the peripheral edge of the opening 23 of the end wall 14 of the barrel and a longitudinal rib 25 to be mated with the longitudinal cutout 24 is provided on the piston rod 3. The length of the rib 25 at least should be arranged such that when the conic body 4a just enters the injection opening 6, the front end of the rib will reach the outer surface of the end wall 14 of the barrel. When the syringe is not in use, the rib 25 is offset from the cutout 24 and an adhesive sealing tape 20 is attached to the end wall 14 of the barrel 1 and the end plate 10 of the piston rod 3 to guard against the case that the syringe, before being used, is rendered useless through inadventer pushing forward the piston to force the conic body 4a to pass through the injection opening 6. During normal use, the injection fluid can be drawn as long as the sealing tape 20 is removed and then injection proceeds, pushing forward the end plate 10 of the piston rod 3. When the front end of the rib reaches the outer surface of the end wall 14 of the barrel, the injector needs only rotate the end plate 10 to align the rib 25 with the cutout 24 (as shown in FIG. 8), and then push further forward the end plate 10 to make the piston 2 glide forward, so that the conic body 4a is made to pass through the injecting opening 6.

The structure of the syringe according to the present invention ensures the syringe to be rendered useless after being used once. That means, it is guaranteed that in case the injector attempts to use the syringe again and forcibly pull the piston rod 3, the syringe will wreck itself. Therefore there is no possibility of reusing the syringe, thus avoiding the disadvantage of conventional syringe in subjecting to cross infection of diseases through reuse.

We claim:

1. A clinical syringe to be rendered useless after being used once, comprising a barrel with a needle fitting hub at the middle of its front end, a piston sealingly and slidably fitted within the barrel and a piston rod connected to the piston, characterized in that a resilient detent plug with a slot thereon is provided at the piston head, an injection opening is defined at a position of the barrel correspondingly to the detent plug, the diameter of which is smaller than the inner diameter of the needle fitting hub, the shape and dimensions of the slot, and the injection opening as well as the resilient detent plug are designated in such a manner that when the piston is pushed forward, the resilient detent plug can easily pass through the injection opening, and when it passes through the opening, the injection fluid can still flow through the injection opening; and when the piston rod is to be retracted after being used once, the detent plug will be retained by the injection opening due to the restoration of the detent plug, and thus unable to get back into the barrel through the opening; said piston rod is a hollow rod with the bore communicating with the outside atmosphere or said piston rod is hollow only at its one end which is connected to the piston, radial apertures joining the piston rod bore with the barrel bore are defined in the hollow part of the rod; the connection between the piston head and the resilient detent plug being so designed that upon retracting the piston rod, ti will easily be destroyed due to the restraining of the detent plug, causing the piston ante-chamber in the barrel to communicate with the piston rear chamber and/or with the outside atmosphere so that the injection fluid can not be drawn.

2. A syringe according to claim 1, characterized in that resilient detent plug is made up of a conic body with a radial dimension at the conic bottom greater than the diameter of the injection opening but smaller than or equal to the inner diameter of the needle fitting hub, and a supporting rod which connects the conic body with said piston head and has a radial dimension smaller than or equal to the diameter of the injection opening, said slot thereof extends from the conic body to within the supporting rod, it has two portions of different width in the radial direction, so that when the resilient detent plug passes through said injection opening and the narrow portion of the slot is squeezed to close, the injection fluid can still be squeezed out from the barrel via the wide portion of the slot.

3. A syringe according to claim 1, characterized in that said resilient detent plug is made up of a conic body with a radial dimension at the conic bottom greater than the diameter of the injection opening but smaller than or equal to the inner diameter of the needle fitting hub, and a supporting rod which connects the conic body with said piston head and has a radial dimension smaller than or equal to the diameter of the injection opening, said slot thereof extends from the conic body to within the supporting rod, one or more longitudinal cutouts are defined on the peripheral edge of said conic body, so that when the conic body passes through said injection opening causing the slot to close, the injection fluid can still be squeezed out from the barrel via said cutout.

4. A syringe according to claim 1, characterized in that said resilient detent plug is made up of a conic body with a radial dimension at the conic bottom greater than the diameter of the injection opening but smaller than the inner diameter of the needle fitting hub , and a supporting rod which connects the conic body with said piston head and has a radial dimension smaller than or equal to the diameter of the injection opening, said slot thereof extends from the conic body to within the supporting rod, one or more longitudinal cutouts are defined on the peripheral edge of the injection opening, so that when the conic body passes through said injection opening causing the slot to close, the injection fluid can still be squeezed out from the barrel via said cutout.

5. A syringe according to claim 1, wherein said resilient detent plug further includes cutouts thereon.

6. A syringe according to any of claims 1-4 or 5, characterized in that said resilient detent plug is preferably formed integral with the piston, a non-through U-shaped notch is punched at the top surface of said piston head adjacent said resilient detent plug to form a U-shaped tongue, so that if the piston is retracted after being used once, the piston head would be torn at the U-shaped notch owing to the retaining of said detent plug 7. A syringe according to any of claims 1-4 or 5, characterized in that said piston head is provided with an opening communicating with the piston rod bore, at the lower end of the resilient detent plug is provided with a thin piece adapted to cover completely said piston opening, the thin piece together with the resilient detent plug is attached hermetically to the piston head; upon retracting the piston rod after being used once, the detent plug will be retained inside the needle fitting hub, and is torn away from the piston head together with the thin piece or the thin piece is damaged.

8. A syringe according to any of claims 1-4 or 5, characterized in that said piston head is provided with an opening communicating with the piston rod bore, some screw threads are provided in said piston opening and at the lower end of the resilient detent plug respectively, so that the detent plug can be sealingly threaded in said opening of the piston head, upon retracting the piston rod at the time when the detent plug is retained inside the needle fitting hub of the barrel, the detent plug would be pulled asunder from said piston opening.

9. A syringe according to any of claims 1-4 or 5, characterized in that said barrel is provided with an end wall with an opening and said piston rod is provided with a flange around it, the position of which is such that when said resilient detent plug gets into the injection opening of the barrel, it is pushed to just reach the outer surface of the end wall of the barrel, so as to remind the user to exert somewhat stronger pushing force in order to push the flange passing through the end wall, thereby forcing the detent plug to pass through the injection opening.

10. A syringe according to any of the claims 1-4 or 5 characterized in that said syringe is provided with an inadvertent push preventive means, which consist of a spacer bar provided between said end wall and an end plate of the piston rod and a dovetail groove defined in said end plate, one end of the spacer bar being connected to said end wall by an resilient connecting means, the free end is designed to have a dovetail shaped tongue with a stop shoulder; the flexibility of the resilient connecting means should enable the spacer bar to be put in a position parallel to the piston rod to make the tongue engage within a dovetail groove defined in said end plate and to position the piston rod by means of the stop shoulder, thus guarding against the case that the syringe, before being used, is rendered useless through inadvertent pushing forward the piston to force the resilient detent plug to push through the injection opening, and upon retracting said end plate to draw in injection fluid and disengage the tongue from the groove, the restoring moment of the resilient connecting means should enable the spacer bar to spring out of its engaging position.

11. A syringe according to claim 10, characterized in that a sealing tape serving as means of position is applied over the end of said barrel and said end plate of said piston rod.

12. A syringe according to any of claim 1-4 or 5, characterized in that said conic body is a circular conic body with said slot located in a symmetry plane of the circular conic body.

* * * * *

UNITED STATES PATENT AND TRADEMARK OFFICE
CERTIFICATE OF CORRECTION

PATENT NO. : 5,106,371
DATED : April 21, 1992
INVENTOR(S) : Mo. Zhao et al.

It is certified that error appears in the above-identified patent and that said Letters Patent is hereby corrected as shown below:

Claim 1, Column 6, Line 5, delete "ti" and substitute therefor --it--.

Claim 2, Column 6, Line 11, after "that" insert --said--.

Signed and Sealed this

Twentieth Day of July, 1993

Attest:

MICHAEL K. KIRK

*Attesting Officer*    Acting Commissioner of Patents and Trademarks